United States Patent
Takizawa

Patent Number: 5,444,237
Date of Patent: Aug. 22, 1995

[54] APPARATUS FOR INSPECTING A BOTTOM BORDER PORTION OF TRANSPARENT GLASS VESSEL FOR A FOREIGN ARTICLE

[75] Inventor: Tsutomu Takizawa, Tokyo, Japan

[73] Assignee: Toyo Glass Company Limited, Tokyo, Japan

[21] Appl. No.: 226,315

[22] Filed: Apr. 12, 1994

[30] Foreign Application Priority Data

Apr. 12, 1993 [JP] Japan ................................ 5-107232

[51] Int. Cl.⁶ ............................................. G01N 9/04
[52] U.S. Cl. .................................. 250/223 B; 250/225; 356/240
[58] Field of Search ............................ 250/223 B, 225; 356/240, 427; 209/526

[56] References Cited

U.S. PATENT DOCUMENTS

| | | | |
|---|---|---|---|
| 4,249,075 | 2/1981 | Lovalenti | 209/526 |
| 4,943,713 | 7/1990 | Yoshida | 250/223 B |
| 5,216,481 | 6/1993 | Minato | 356/240 |

Primary Examiner—David C. Nelms
Assistant Examiner—J. Steady
Attorney, Agent, or Firm—Sughrue, Mion, Zinn, Macpeak & Seas

[57] ABSTRACT

An inspection apparatus which automatically inspects a bottom border portion of a transparent glass vessel for a foreign article accurately is disclosed. Light is projected and received by way of first and second polarization filters through a rotating glass vessel to image the vessel obliquely from below by a solid state image pickup elements of a camera. Brightness values of outputs of the elements of the camera are compared with threshold values for binary digitization and determined as abnormality values when they are higher. The threshold values are varied and the abnormality values are corrected in accordance with the positions of the elements of the camera, and then presence or absence of a foreign article is determined from the corrected abnormality values or the sum of them.

3 Claims, 4 Drawing Sheets (1)

(2) (3)

(4) (5)

(6)

APPARATUS FOR INSPECTING A BOTTOM BORDER PORTION OF TRANSPARENT GLASS VESSEL FOR A FOREIGN ARTICLE

BACKGROUND OF THE INVENTION

1. Field of the Invention

This invention relates to an apparatus for inspecting a bottom border portion (a circumferential corner portion of the bottom and a portion around the circumferential corner portion) of a transparent glass vessel to check whether or not a foreign article is present in the glass material of the bottom border portion. It is to be noted that, in the present specification, the terminology "transparent glass vessel" is intended to include not only literal transparent glass vessels but also translucent glass vessels and may be colorless or colored.

2. Description of the Related Art

Apparatus for inspecting a glass vessel for a foreign article which are used popularly are roughly divided into two types including an inspection apparatus which is used to principally inspect a body portion of a vessel and includes a diffusion light source and a solid state image pickup element camera arranged in a horizontally opposing relationship to each other with a vessel as an object for inspection interposed between them and another inspection apparatus which is used to principally inspect a bottom portion of a vessel and includes a diffusion light source and a solid state image pickup element camera arranged in a vertically opposing relationship to each other with a vessel as an object for inspection interposed between them.

However, It is actually difficult to inspect a bottom border portion of a glass vessel using an inspection apparatus of the horizontal arrangement type since, at a bottom portion of a vessel, the light path along which light from a light source passes through the glass material is comparatively long and attenuation of the light there is so great that, if the bottom portion is curved, then the light cannot pass through it due to refraction there.

Meanwhile, with an inspection apparatus of the vertical arrangement type, a bottom portion of a vessel is imaged by a camera through a mouth portion of the vessel. However, it is difficult to inspect a bottom border portion (a bottom circumferential corner portion and around such portion) due to reflection of light at an inner wall face of the vessel or refraction of light caused by a variation in shape, and particularly for a vessel having a small mouth, since the field of view of the camera to the bottom portion of the vessel is narrowed by the small mouth, a bottom circumferential corner portion cannot be inspected with the inspection apparatus of the vertical arrangement type.

By the way, cullet (fragments of glass) collected from the city is recycled as a raw material for glass vessels as a part of recycling of glass vessels. However, such cullet collected from the city normally contains a large amount of substances, for example, pottery, porcelain, metals such as aluminum, and heat resisting glass other than a raw material of glass for glass vessels to be recycled, and therefore, it is tried to remove such substances to the utmost. However, since they cannot be removed completely, they remain as foreign articles in a glass vessel as a product.

Where such foreign articles are present in a body portion or a bottom portion of a glass vessel, they can be found out almost by an inspection apparatus of the horizontal type or the vertical type described above, and accordingly, particularly at a content filling step after shipment of products of glass vessels, an accident of breakage caused by a foreign article present in a bottom portion or a bottom portion of a glass vessel seldom occurs. However, since a foreign article in a bottom border portion of a glass vessel cannot be found out with a conventional inspection apparatus as described hereinabove, although the bottom border portion has a greater thickness of material than the other portions of the glass vessel, it is a situation at present that accidents of breakage at the bottom border portion arising from presence of a foreign article there increase as the amount of use of collected cullet increases.

SUMMARY OF THE INVENTION

It is an object of the present invention to provide an inspection apparatus for a foreign article which can automatically perform inspection to determine whether a foreign article is present at a bottom border portion of a transparent glass vessel such as a glass bottle.

In order to attain the object described above, according to the present invention, there is provided an apparatus for inspecting a bottom border portion of a transparent glass vessel for a foreign article, which comprises rotation means for rotating a transparent glass vessel around a vertical axis at an inspection position, a diffusion light source, a first polarization filter arranged in front of the diffusion light source and having a vertical optical axis for polarizing light from the diffusion light source and projecting the polarized light upon the transparent glass vessel, a solid state image pickup element camera disposed with an angle of depression with respect to the axis of the transparent glass vessel for imaging a bottom border portion of the transparent glass vessel obliquely from below on the opposite side to the first polarization filter with respect to the transparent glass vessel, a second polarization filter having a polarization axis perpendicular to that of the first polarization filter and arranged for introducing the light polarized by and transmitted through the transparent glass vessel into the solid state image pickup element camera, image fetching means for fetching outputs of solid state image pickup elements of the solid state image pickup element camera at a period conforming to a speed of rotation of the transparent glass vessel by the rotation means, storage means for storing the outputs thus fetched as digital values for at least one rotation of the transparent glass vessel, abnormal value detection means for comparing the digital values upon fetching in magnitude with threshold values set for the individual solid state image pickup elements in accordance with their positions and determining the numbers of times by which the threshold values are exceeded as abnormality values, correction means for multiplying the abnormality values by correction coefficients determined in accordance with the positions of the solid state image pickup elements, and foreign article presence/absence determination means for determining presence or absence of a foreign article in the transparent glass vessel from the abnormality values after corrected.

Preferably, the angle of depression of the solid state image pickup element camera is 50 to 60 degrees, more preferably about 55 degrees.

Preferably, the foreign article presence/absence determination means sums up the abnormality values after corrected only for a preset inspection area and compares the sum value with a prescribed value to determine presence or absence of a foreign article.

When light from the diffusion light source is projected upon a transparent glass vessel through the first polarization filter to pick up an image of a bottom border portion of the transparent glass vessel obliquely from below by means of the solid state image pickup element camera, although the bottom border portion exhibits a great variation in shape at inner and outer faces thereof, an image formed from transmission light can be picked up without producing a shadow caused by refraction of the glass.

The light from the diffusion light source is vertically polarized by the first polarization filter, and when no foreign article is present in the transparent glass vessel within the field of view of the camera, the transmission light through the glass vessel is intercepted by the second polarization filter. Consequently, no bright portion appears in the image picked up by the camera. In contrast, when a foreign article is present at the bottom border portion of the glass vessel, light which is transmitted through a distorted portion of the glass vessel around the foreign article is polarized there and is transmitted through the second polarization filter without being intercepted by the same so that it appears as a bright portion in the image picked up by the camera. Since such bright portion arises from the transmission light from the portion of the transparent glass vessel around the foreign article, it is observed as an image larger than the image of the foreign article itself.

Since an image of the bottom border portion of the glass vessel is picked up obliquely from below by the solid state image pickup element camera, as viewed from the camera, the length of the path of light transmitted through the glass vessel is different at different locations and also the degree of attenuation of the transmission light is different. Further, where such a convex or concave portion as a character or a design pattern is present on an outer face of the bottom of the glass vessel, weak light which is not produced by polarization may possibly enter the camera due to refracted light or reflected light by such portion. In order to cope with such circumstances, the threshold value which is used to determine and binary digitize an output (brightness level) of a solid state image pickup element of the camera must necessarily be varied for each of the solid state image pickup elements in accordance with the position of it on the glass vessel.

Further, according to the present invention, since, while the glass vessel is being rotated, an image of the bottom border portion of the glass vessel is picked up obliquely from below by means of the solid state image pickup element camera and the outputs of the solid state image pickup elements of the camera are fetched at a period conforming to the speed of rotation of the vessel, also the time for which transmission light originating from a foreign article enters the field of view of the camera depends upon the position of the foreign article, and even if the foreign article is same in size, the speed of movement of the foreign article is lower and the time within which the foreign article remains within the field of view is longer as the position of the foreign article is nearer to the center of the bottom. On the contrary as the foreign article is nearer to a bottom border portion, the speed of movement is higher and the time within which the foreign article remains within the field of view is shorter. In other words, even if the size of the foreign article is equal, the size of the bright portion in the picked up image of the camera is different depending upon the difference in position of the foreign article on the glass vessel. In the present invention, since the numbers of times by which the digital values upon fetching of the outputs of the solid state image pickup elements of the camera exceed the threshold values are determined as abnormality values, that is, the size of the bright portion, the difference in size of the bright portion which arises from the difference in position is compensated for by correction of the abnormality values and presence or absence of a foreign article is determined from the thus corrected values. By such means, an article sticking to the surface of the object for inspection or a convex or concave design pattern which is imaged apparently with a greater size because it is located close to the center of the bottom and has such a brightness that exceeds a threshold value upon binary digitization is eliminated, and wrong determination caused by such article or convex or concave design pattern can be prevented.

In summary, with the inspection apparatus of the present invention, with attention paid to the fact that, when a foreign article is present in a bottom border portion of a transparent glass vessel, light is polarized by a distorted portion of the transparent glass material around the foreign article, light is projected and received by way of the first and second polarization filters, and although the transparent glass vessel is imaged obliquely from below while it is being rotated in order to facilitate imaging of the bottom border portion by the solid state image pickup elements of the camera, the threshold values for binary digitization of the outputs of the solid state image pickup elements are varied and abnormality values which are degrees of excess of brightness values above the threshold values are corrected in accordance with the positions of the solid state image pickup elements and then presence or absence of a foreign article is determined from the sum of the abnormality values. Consequently, the determination can be performed accurately separately from a character, a convex or concave portion or the like other than a foreign article. Accordingly, since inspection for a foreign article of a bottom border portion, which has been a blind point till now, can be performed with a high degree of accuracy, accidents of breakage particularly at a contents filling step can be reduced, and the uneasiness when cullet collected from the city is used can be eliminated. Consequently, the inspection apparatus can promote increase of the amount of use of such cullet and contribute to enhancement of recycling of glass vessels.

The above and other objects, features and advantages of the present invention will become apparent from the following description and the appended claims, taken in conjunction with the accompanying drawings in which like parts or elements are denoted by like reference characters.

DETAILED DESCRIPTION OF THE PREFERRED EMBODIMENT

Figure 1:
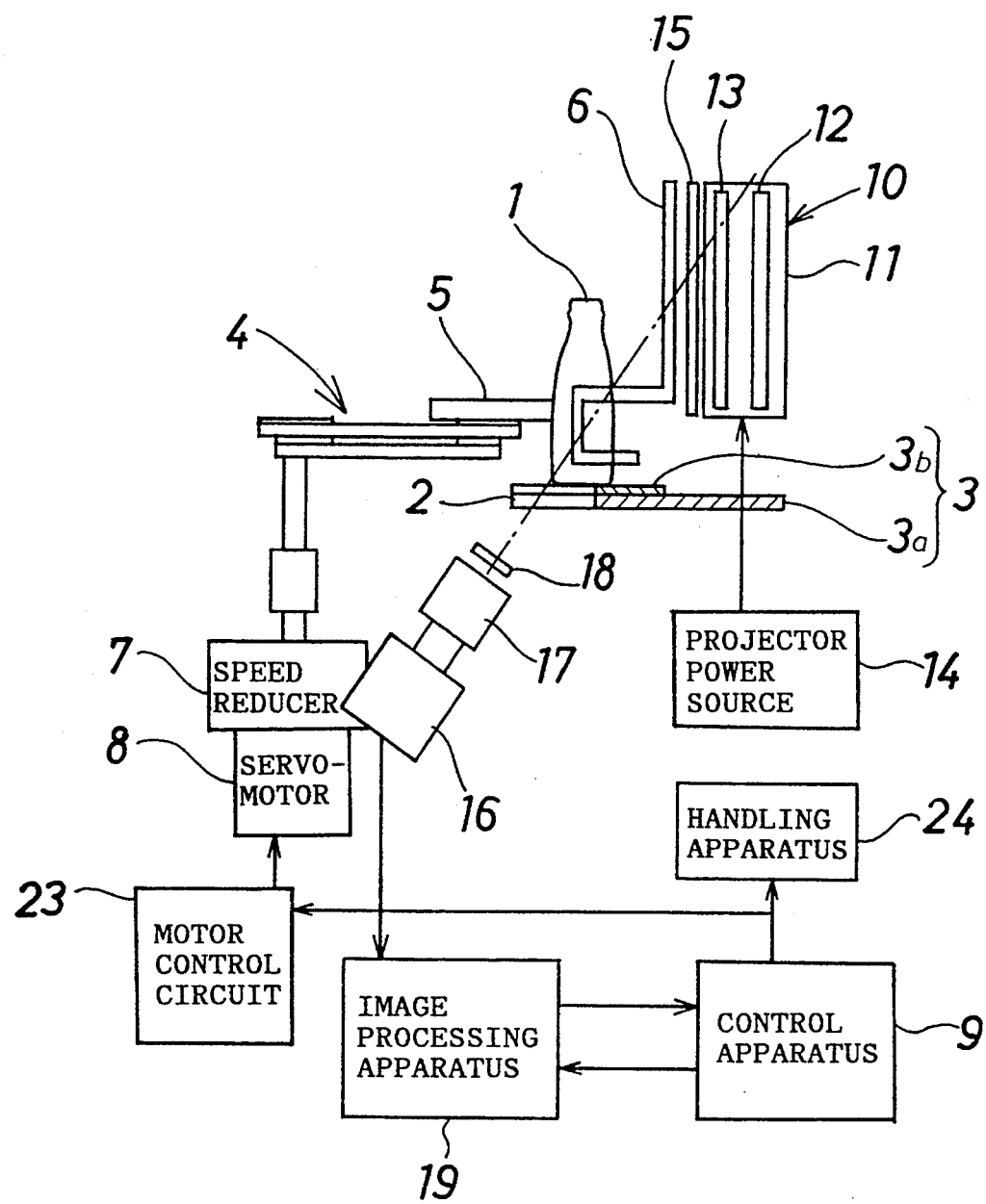
FIG. 1 is a schematic block diagram of an inspection apparatus for a foreign article according to the present invention.

Referring first to FIG. 1, there is shown an inspection apparatus for a foreign article to which the present invention. The inspection apparatus shown includes a transparent glass vessel 1 in the form of a glass bottle which is an object for inspection and has been transported onto an inspection table 3 by transport means not shown. The inspection table 3 has an inspection window 2 formed therein. The transparent glass vessel 1 is rotated around an axis thereof on the inspection table 3 by a rotation apparatus 4 while it is held erected uprightly. In this instance, the transparent glass vessel 1 is rotated while it is positioned between a rotation disk 5 and a holder 6, and the rotation disk 5 is rotated by a servomotor 8 by way of a speed reducer 7 while the speed of rotation thereof is detected by a control apparatus 9 in the form of a computer. The inspection table 3 includes a fixed lower plate 3a made of aluminum or a like metal, and an upper plate 3b made of a plastics material and mounted for sliding movement on the lower plate 3a.

A projector 10 serving as a diffusion light source is installed at a location obliquely upwardly of the inspection table 3. The projector 10 includes a fluorescent lamp 12 accommodated in a box 11, a diffusion plate 13 for diffusing light from the fluorescent lamp 12, and a projector power source 14 including a high frequency or dc lighting circuit for preventing flickering of the fluorescent lamp 12. A first polarization filter 15 having a vertical polarization axis parallel to the axis of the transparent glass vessel 1 is disposed in front of the diffusion plate 13 so that diffusion light from the projector 10 is vertically polarized by the polarization filter 15 and irradiated upon the transparent glass vessel 1 from obliquely above.

Figure 2:
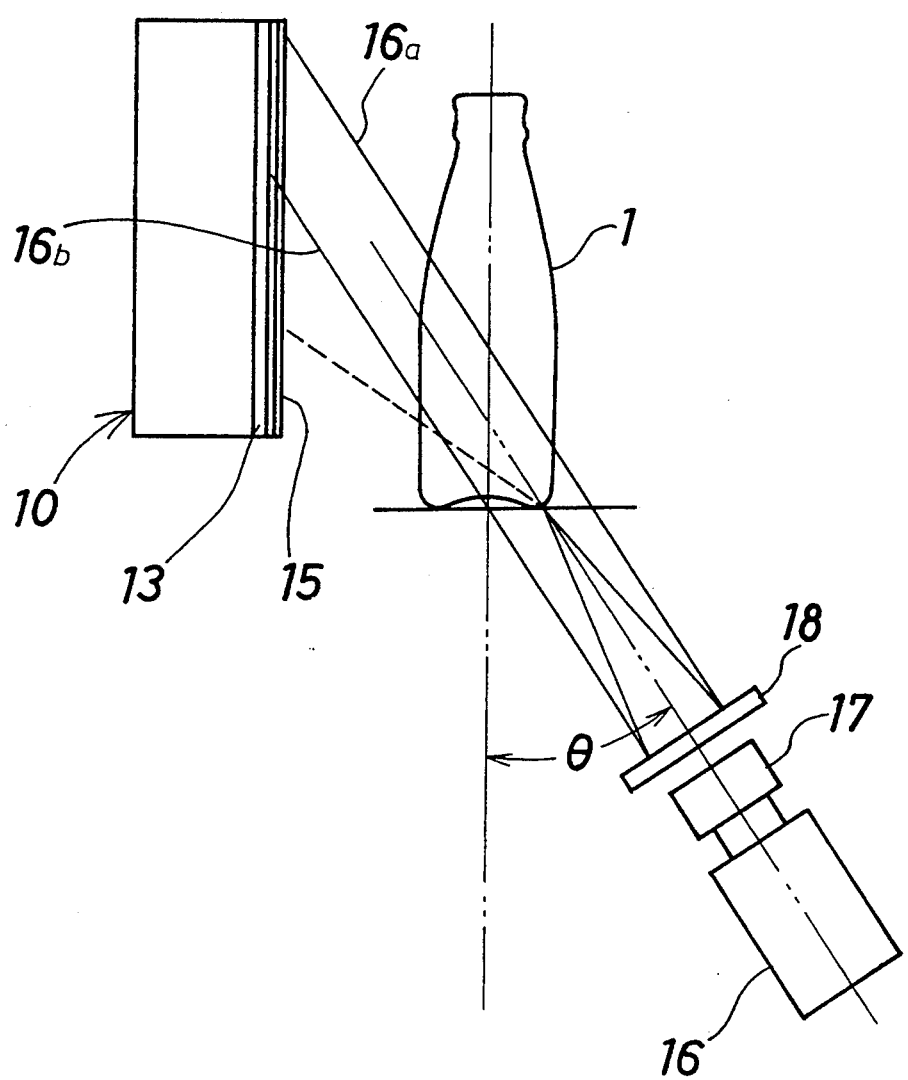
FIG. 2 is a schematic view illustrating the positional relationship among a projector, a transparent glass vessel, and a solid state image pickup element camera of the inspection apparatus shown in FIG. 1.

Meanwhile, installed at a location obliquely downwardly of the inspection table 3 is a solid state image pickup element camera 16 in the form of a CCD (charge coupled device) line image sensor which is directed so that it may pickup an image of a bottom border portion of the transparent glass vessel 1 on the inspection table 3 from obliquely below. As seen in FIG. 2, the angle $\theta$ of depression of the camera 16, that is, the angle of the direction of the camera 16 with respect to the axis of the transparent glass vessel 1 on the inspection table 8, is set to 50 to 60 degrees, preferably to about 55 degrees in order to avoid refraction light or reflection light from any other portion of the transparent glass vessel 1 than a foreign article to be detected. Further, in order that also upper and lower peripheral portions around the circumferential corner portion of the bottom of the transparent glass vessel 1 may be included in an inspection area, the projector 10 is set such that the top end of the projection area of diffusion light thereof is positioned above an extension line 16a of the top end of the field of view of the camera 16 and the bottom end of the projection area of the diffusion light of the projector 10 is positioned, taking a comparatively great amount of reflection at the circumferential corner portion of the bottom of the transparent glass vessel 1, below an extension line 16b of the bottom end of the field of view of the camera 16 with a sufficient margin provided between them.

A condenser lens 17 is disposed in front of the camera 16, and a second polarization filter 18 is disposed in front of the condenser lens 17. The polarization filter 18 has a polarization axis perpendicular to that of the first polarization filter 15 described above so that only that portion of light polarized by the first polarization filter 15 and irradiated upon the transparent glass vessel 1 which is further polarized by and transmitted through the transparent glass vessel 1 is transmitted through the second polarization filter 18 and enters the camera 16.

Figure 3:
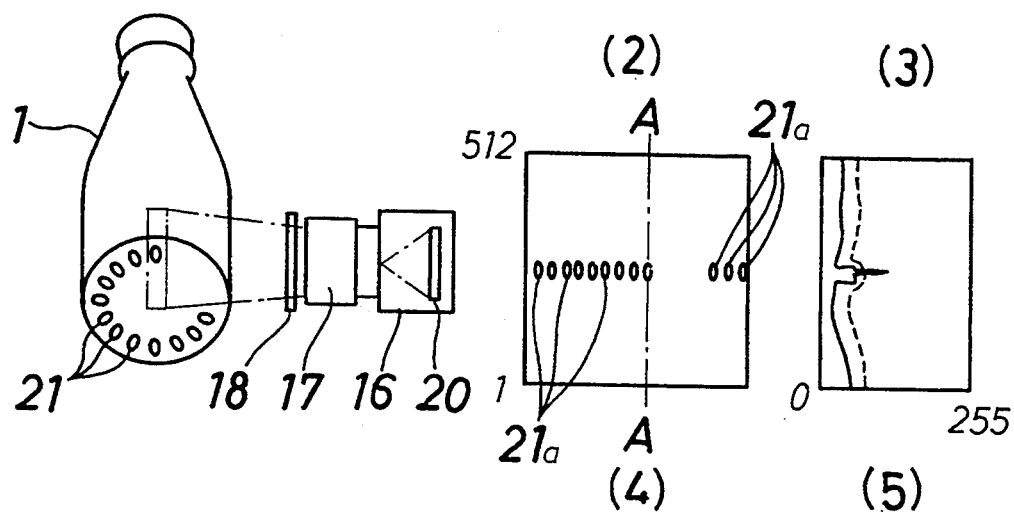
FIG. 3 is a diagrammatic view showing different image processing steps in (1) to (6) when a transparent glass vessel inspected is an acceptable article free from a foreign article.
Figure 3:
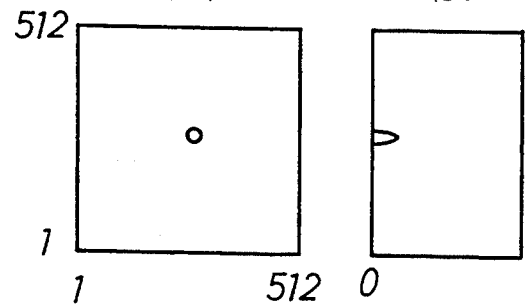
Figure 3:
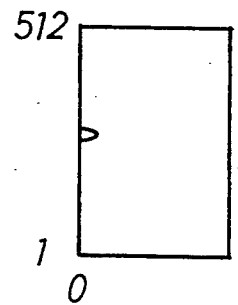

An image processing apparatus 19 including a CPU (central processing unit), a memory and so forth not shown is connected to the camera 16, and as shown in (1) of FIG. 3, outputs of a set of solid state image pickup elements, 512 elements in the present embodiment, of a line image sensor 20 of the camera 16 are fetched into the image processing apparatus 19 at a period conforming to the speed of rotation of the transparent glass vessel 1 in response to a timing signal from the control apparatus 9. The outputs thus fetched are converted into digital values and stored into the memory of the image processing apparatus 19 by a prescribed number of times (for example, 512) for the time while the transparent glass vessel 1 completes one rotation. In short, picked up image data for one rotation of the transparent glass vessel 1 are stored as digital data into the memory in such a fashion that they are developed on a screen in a sense. (2) of FIG. 3 is a schematic view of an image (analog image) of such screen, and the axis of ordinate coincides with the direction of arrangement of the 512 solid state image pickup elements of the line image sensor 20 while the axis of abscissa corresponds to the direction in which fetching of the 512 outputs proceeds.

After fetching and storage for one rotation are completed, the image processing apparatus 19 compares the data for one screen, that is, 512×512 data, stored in the memory thereof with respective threshold values which are determined differently in accordance with the positions of the solid state image pickup elements of the camera 16 to binary digitize the data. (3) of FIG. 3 indicates the brightness levels of the solid state image pickup elements upon fetching along line A—A in (2) of FIG. 3 in an analog fashion, and such threshold values as indicated by a broken line are set in order to binary digitize the brightness levels. In this instance, where a character or a convex or concave portion is embossed at a particular location of the transparent glass vessel 1 and refracted light or reflected by such character or convex or concave portion is imaged as a bright portion of a low brightness by the camera 16, the threshold values for the corresponding portion are set somewhat higher than those for the other portions so that such character or convex or concave portion can be eliminated as it is outside the object for inspection.

FIG. 3 illustrates the image processing steps when the transparent glass vessel 1 as an object for inspection is an acceptable article and shows that a plurality of protruded portions 21 representative of a model number code or the like are provided on the same circumferential line as shown in (1) of FIG. 3 and images 21a of the protruded portions 21 appear as shown in (2) of FIG. 3 on the screen. Since the brightness values of such images 21a are low, they can be eliminated in most cases by binary digitization processing of them. However, it possibly occurs that the brightness may partially exceed threshold values for binary digitization as shown in (3)

of FIG. 3 and an image there remains present as seen in (4) of FIG. 3 even after binary digitization processing is performed. However, such a low brightness portion which does not originate from a foreign article can be eliminated by a process which will be hereinafter described.

Figure 4:
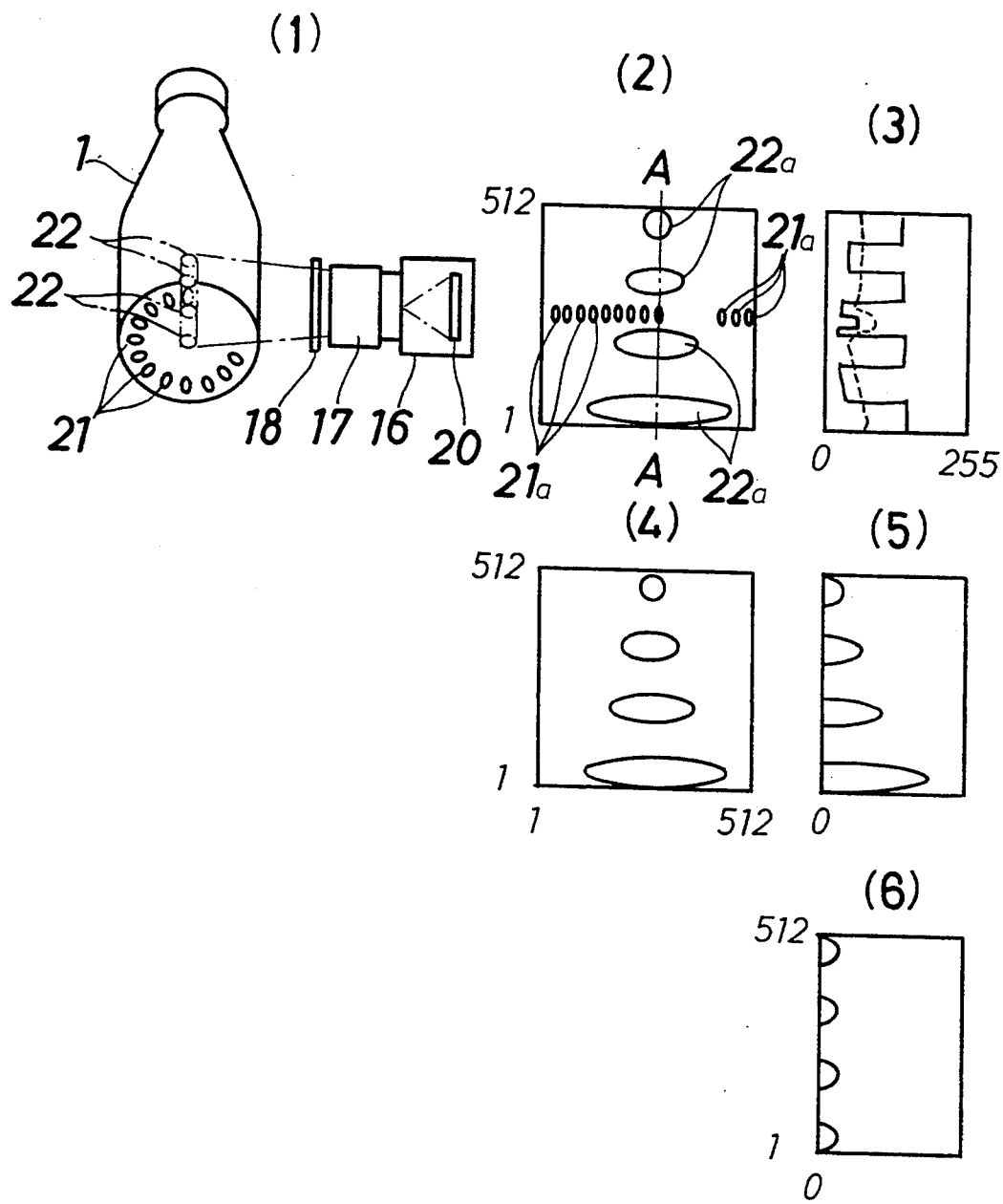
FIG. 4 is a similar view but showing different image processing steps when a transparent glass vessel inspected has a foreign article.

FIG. 4 illustrates the image processing steps when the transparent glass vessel 1 as an object for measurement is a defective article which has such a foreign article 22 as shown in (1) at a bottom border portion thereof. In this instance, images 22a originating from such foreign articles 22 have a high brightness as shown in (2) of FIG. 4, and if they are binary digitized as shown in (3) of FIG. 4, then most of them remain as shown in (4) of FIG. 4.

The image processing apparatus 19 counts, after binary digitization, the numbers of times by which the threshold values are exceeded for the individual solid state image pickup elements of the camera 16 and stores them as abnormality values in a sense. (5) of FIG. 3 shows that one of the images 21a of the protruded portions 21 described above remains even after binary digitization because the brightness is high and this is detected as a low abnormality value. On the other hand, (5) of FIG. 4 shows that the images 22a originating from the foreign articles 22 are detected as high abnormality values.

Since the transparent glass vessel 1 is imaged obliquely from below by the camera 16 while it is being rotated as described above, the size of the image is apparently different due to the difference in position among the solid state image pickup elements of the line image sensor 20 of the camera 16, and accordingly, deviations of abnormality values arising from the difference in positions of the solid state image pickup elements are produced among the solid state image pickup elements. Therefore, in order to compensate for such deviations, the image processing apparatus 19 multiplies the abnormality values by correction coefficients determined in advance in accordance with the positions of the solid state image pickup elements to effect abnormality value correction (area correction of a bright portion after binary digitization). (6) of FIG. 3 shows that abnormality value correction has been performed for (5) of FIG. 3, and (6) of FIG. 4 shows that abnormality value correction has been performed for (5) of FIG. 4.

Thereafter, the image processing apparatus 19 sums the thus corrected abnormality values for the predetermined inspection area within one screen (for one rotation of the transparent glass vessel 1), and compares the sum value (total area of the brightness portion or portions after binary digitization) with a prescribed value. If the sum value exceeds the prescribed value, then the image processing apparatus 19 determines that the transparent glass vessel 1 is a defective article (having a foreign article), but if the sum value does not exceed the prescribed value, then the image processing apparatus 19 determines that the transparent glass vessel 1 is an acceptable article having no foreign article, and the image processing apparatus 19 sends a signal representative of a result of the determination to the control apparatus 6. The control apparatus 19 having received the signal sends an inspection completion signal for one transparent glass vessel to a motor control circuit 23 for controlling the servomotor 8, and when the transparent glass vessel 1 is a defective article, the control apparatus 19 sends an exclusion signal to a handling apparatus 24 to exclude the transparent glass vessel of the defective article. Since, if the corrected abnormality values are summed, then a small bright portion of a high brightness of an acceptable article of FIG. 3 which does not originate from a foreign article and remains up to the stage of (6) of FIG. 3 is eliminated, the transparent glass article in this instance is not determined as a defective article.

Having now fully described the invention, it will be apparent to one of ordinary skill in the art that many changes and modifications can be made thereto without departing from the spirit and scope of the invention as set forth herein.

What is claimed is:

1. An apparatus for inspecting a bottom border portion of a transparent glass vessel for a foreign article, comprising:

rotation means for rotating a transparent glass vessel around a vertical axis at an inspection position;

a diffusion light source;

a first polarization filter arranged in front of said diffusion light source and having a vertical optical axis for polarizing light from said diffusion light source and projecting the polarized light upon the transparent glass vessel;

a solid state image pickup element camera disposed with an angle of depression with respect to the axis of the transparent glass vessel for imaging a bottom border portion of the transparent glass vessel obliquely from below on the opposite side to said first polarization filter with respect to the transparent glass vessel;

a second polarization filter having a polarization axis perpendicular to that of said first polarization filter and arranged for introducing the light polarized by and transmitted through the transparent glass vessel into said solid state image pickup element camera;

image fetching means for fetching outputs of solid state image pickup elements of said solid state image pickup element camera at a period conforming to a speed of rotation of the transparent glass vessel by said rotation means;

storage means for storing the outputs thus fetched as digital values for at least one rotation of the transparent glass vessel;

abnormal value detection means for comparing the digital values upon fetching in magnitude with threshold values set for the individual solid state image pickup elements in accordance with their positions and determining the numbers of times by which the threshold values are exceeded as abnormality values;

correction means for multiplying the abnormality values by correction coefficients determined in accordance with the positions of the solid state image pickup elements; and foreign article presence/absence determination means for determining presence or absence of a foreign article in the transparent glass vessel from the abnormality values after corrected.

2. An apparatus for inspecting a bottom border portion of a transparent glass vessel for a foreign article as claimed in claim 1, wherein the angle of depression of said solid state image pickup element camera is 50 to 60 degrees, preferably about 55 degrees.

3. An apparatus for inspecting a bottom border portion of a transparent glass vessel for a foreign article as claimed in claim 1, wherein said foreign article presence/absence determination means sums up the abnormality values after corrected only for a preset inspection area and compares the sum value with a prescribed value to determine presence or absence of a foreign article.

* * * * *